(12) United States Patent
Knappe et al.

(10) Patent No.: US 8,235,402 B2
(45) Date of Patent: Aug. 7, 2012

(54) COUPLING DEVICE OF A TRANSPORT CART WITH A STRUCTURE OF A SUPPLY PANEL FOR MEDICAL APPLICATIONS

(75) Inventors: Stefan Knappe, Burghaun (DE); Matthias Weller, Rosdorf (DE)

(73) Assignee: Ondal Holding GmbH, Hunfeld (DE)

( * ) Notice: Subject to any disclaimer, the term of this patent is extended or adjusted under 35 U.S.C. 154(b) by 341 days.

(21) Appl. No.: 12/446,204

(22) PCT Filed: Oct. 18, 2007

(86) PCT No.: PCT/EP2007/009058
§ 371 (c)(1),
(2), (4) Date: Apr. 6, 2010

(87) PCT Pub. No.: WO2008/046631
PCT Pub. Date: Apr. 24, 2008

(65) Prior Publication Data
US 2010/0187785 A1    Jul. 29, 2010

(30) Foreign Application Priority Data
Oct. 19, 2006 (EP) .................................... 06122617

(51) Int. Cl.
*B62B 3/00* (2006.01)
(52) U.S. Cl. ................. 280/47.34; 280/47.35; 280/47.26

(58) Field of Classification Search ............... 280/47.26, 280/47.35, 35, 292, 79.2, 79.3, 47.33, 47.34; 248/229.16, 231.71, 214, 129
See application file for complete search history.

(56) References Cited

U.S. PATENT DOCUMENTS

| | | | | | |
|---|---|---|---|---|---|
| 4,511,158 | A | * | 4/1985 | Varga et al. ................... | 280/292 |
| 5,326,059 | A | * | 7/1994 | Pryor et al. ............. | 248/231.71 |
| 5,344,169 | A | * | 9/1994 | Pryor et al. .................. | 280/79.3 |
| 5,556,065 | A | * | 9/1996 | Wadley ......................... | 248/129 |
| 5,588,166 | A | * | 12/1996 | Burnett ......................... | 248/214 |
| 6,179,260 | B1 | * | 1/2001 | Ohanian .................. | 248/229.16 |
| 6,213,481 | B1 | * | 4/2001 | Marchese et al. ............... | 280/35 |
| 6,708,991 | B1 | * | 3/2004 | Ortlieb ........................ | 280/47.26 |
| 6,725,483 | B2 | | 4/2004 | Gallant et al. | |

FOREIGN PATENT DOCUMENTS
DE            10219221 A1    5/2003
* cited by examiner

*Primary Examiner* — Hau Phan
(74) *Attorney, Agent, or Firm* — Seed IP Law Group PLLC (57) ABSTRACT

A coupling device of a transport cart, through which the transport cart can be coupled to a structure of a supply panel for medical applications, wherein the supply panel can be positioned through a ceiling mount. The coupling device has a first and a second jaw that can be coupled to the structure of the supply panel, wherein, in order to couple the transport cart to the structure, the first jaw, via a first latching device, and the second jaw, via a second latching device, can be locked into a closed position (FIG. 6) from a stopped, uncoupled open position upon mechanical pressure contact with the structure.

7 Claims, 10 Drawing Sheets

COUPLING DEVICE OF A TRANSPORT CART WITH A STRUCTURE OF A SUPPLY PANEL FOR MEDICAL APPLICATIONS

BACKGROUND

Technical Field

The invention relates to a coupling device, and, particularly to a device for coupling a cart to a structure.

BRIEF SUMMARY

An object of at least one embodiment of the invention is to obtain a coupling device of a transport cart through which the transport cart can be coupled to a structure of a supply panel for medical applications, wherein the supply panel can be positioned through a ceiling mount; said coupling device enables easy coupling and decoupling. As an additional object of the invention, the generically equivalent coupling device should enable functionally secure coupling.

With the aid of the coupling device according to embodiments of the invention, a transport cart can be coupled to a structure (e.g., support pipes of a multifunctional rack) of a supply panel with the easiest of handling. The supply panel can thereby be moved or positioned by the user horizontally in the room. The connection (coupling) of the two components, transport cart/supply panel, remains in place as long as it is not disassembled by the user. The coupling device ensures that the coupled transport cart automatically executes the movements of the supply panel in the room without requiring any additional activity on the part of the operator or user.

In certain embodiments, an interlocking device also enables functionally secure coupling of the transport cart to the supply panel. This ensures that "single-sided" coupling is not possible, because the coupling device does not lock as long as only one side of the coupling device is routed on the support pipe. Not until both jaws of the coupling device make contact with the support pipes is the coupling process released and the jaws of the coupling device are automatically closed.

The invention is described in more detail using an exemplary embodiment.

BRIEF DESCRIPTION OF THE SEVERAL VIEWS OF THE DRAWINGS

The following is shown.

DETAILED DESCRIPTION

Figure 1:
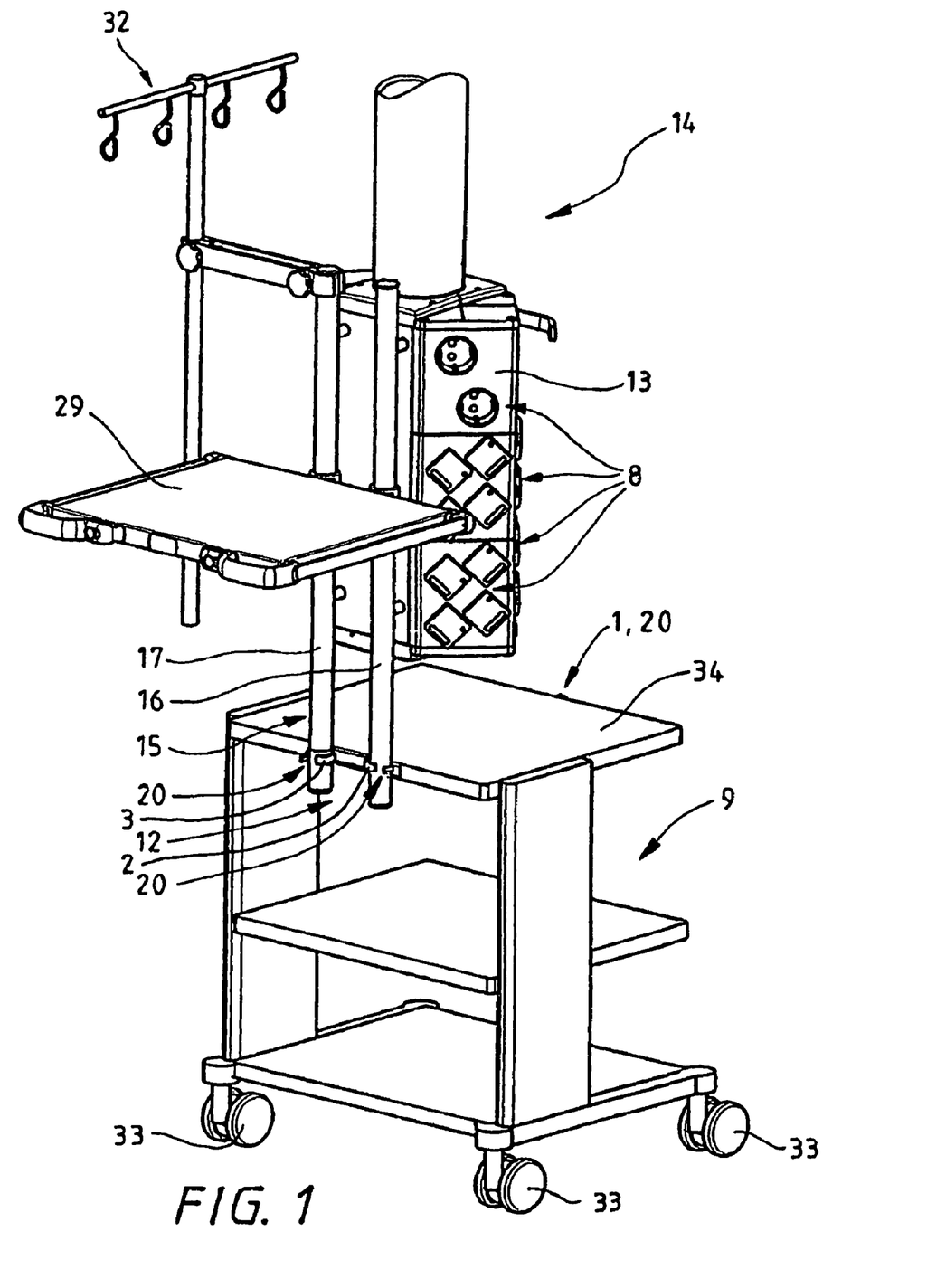
FIG. 1 shows a perspective view of a transport cart that is connected to a structure of a supply panel using one embodiment of a coupling device.

FIG. 1 shows a coupling device 12 of a transport cart 9 through which the transport cart 9 can be coupled to a structure 15 (first and second support rod 16, 17) of a supply panel 13 for medical applications. Four wheels 33 are arranged to facilitate movement of the coupled transport cart 9. The structure 15 in this case is provided, for example, to hold a tray 29 and a drip stand 32. The supply panel 13 has various groups of supply connections 8 (gas, current, etc.) and can be positioned vertically or horizontally in a room via a schematically shown ceiling mount 14. The coupling device 12 has two jaws 2, 3 that can be coupled to the structure 15 of the supply panel 13. In order to couple the transport cart 9 to the structure 15, both jaws 2, 3 automatically snap into a closed position 20 (FIG. 7) from a stopped, uncoupled opened position 19 (FIG. 6), using a latching device 18.1, 18.2, upon mechanical pressure contact with the structure 15.

The symmetrical construction of the coupling device 12 enables economical manufacturing, because only one set of single parts is required.

Figure 2:
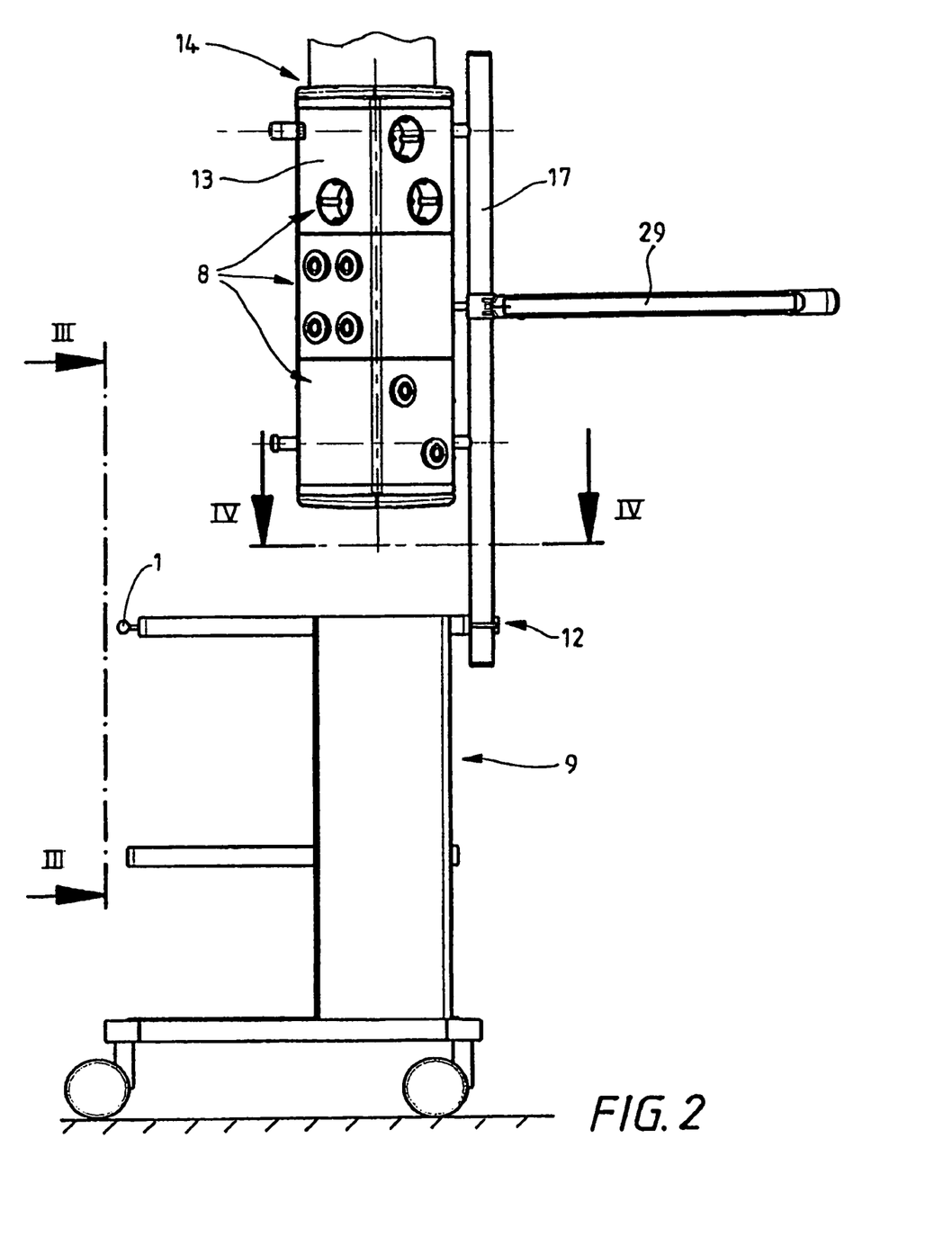
FIG. 2 shows a side view of the transport cart with the supply panel according to FIG. 1.

FIG. 2 shows a side view of the transport cart 9 with the supply panel 13 according to FIG. 1.

Figure 3:
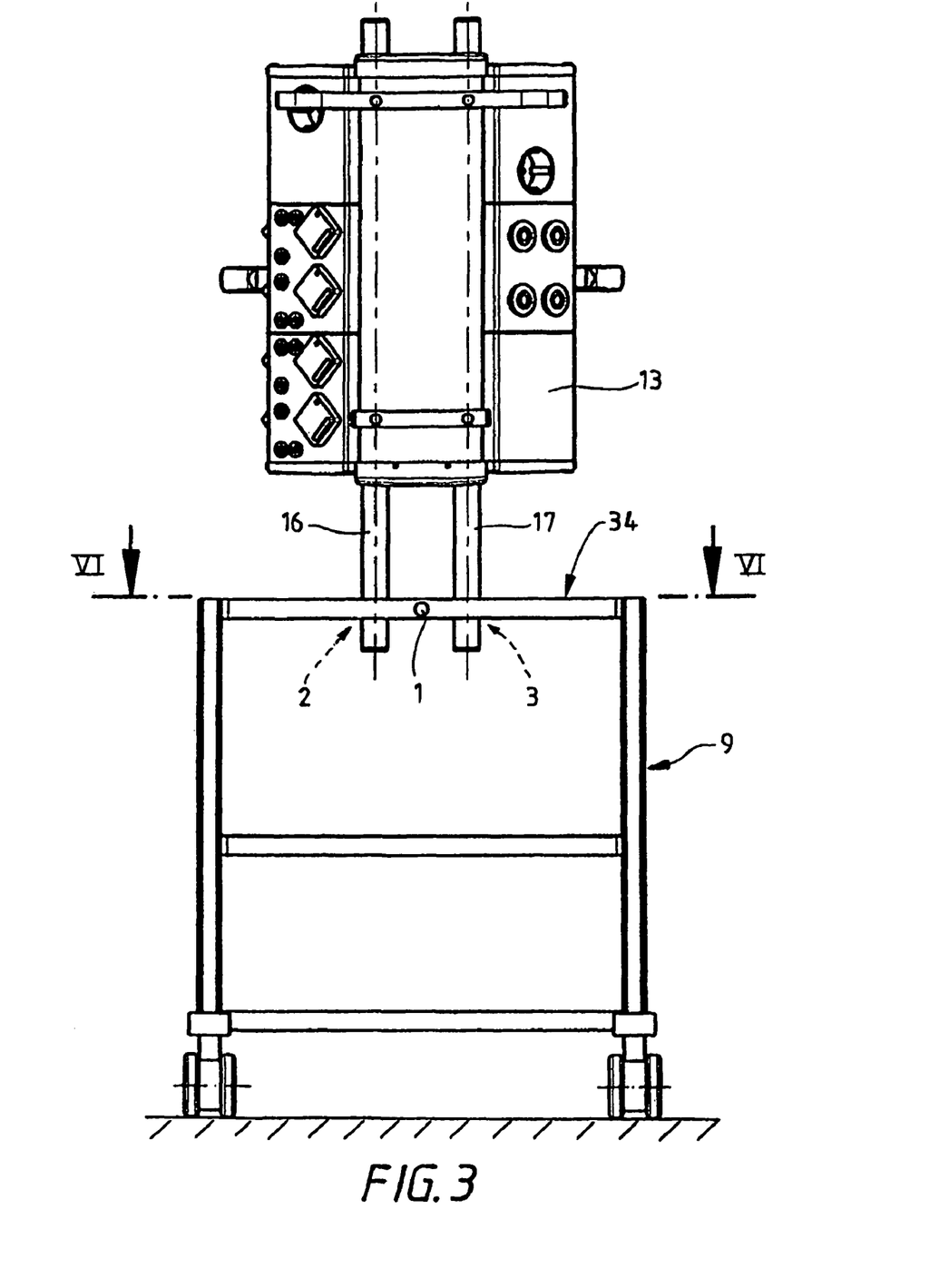
FIG. 3 shows a side view III-III of the transport cart with the supply panel according to FIG. 2.

FIG. 3 shows a side view III-III of the transport cart 9 with the supply panel 13 according to FIG. 2.

Figure 4:
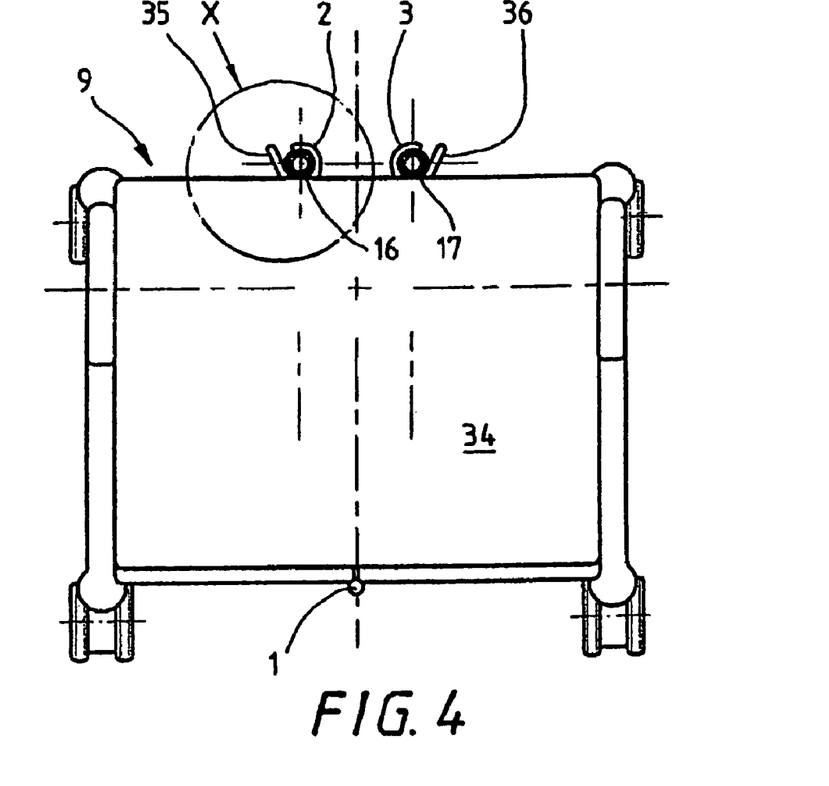
FIG. 4 shows a sectional view IV-IV of the transport cart according to FIG. 2.

FIG. 4 shows a sectional view IV-IV of the transport cart 9 according to FIG. 2.

Figure 5:
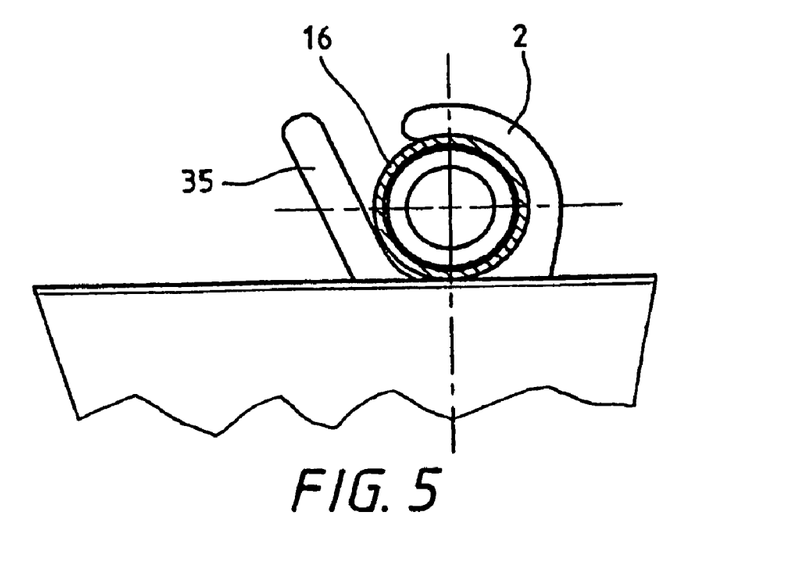
FIG. 5 shows a detailed view X according to FIG. 4 of a jaw coupled to the structure.

FIG. 5 shows an enlarged detailed view X according to FIG. 2 of a first jaw 2 coupled to support rod 16 of the structure 15.

Figure 6:
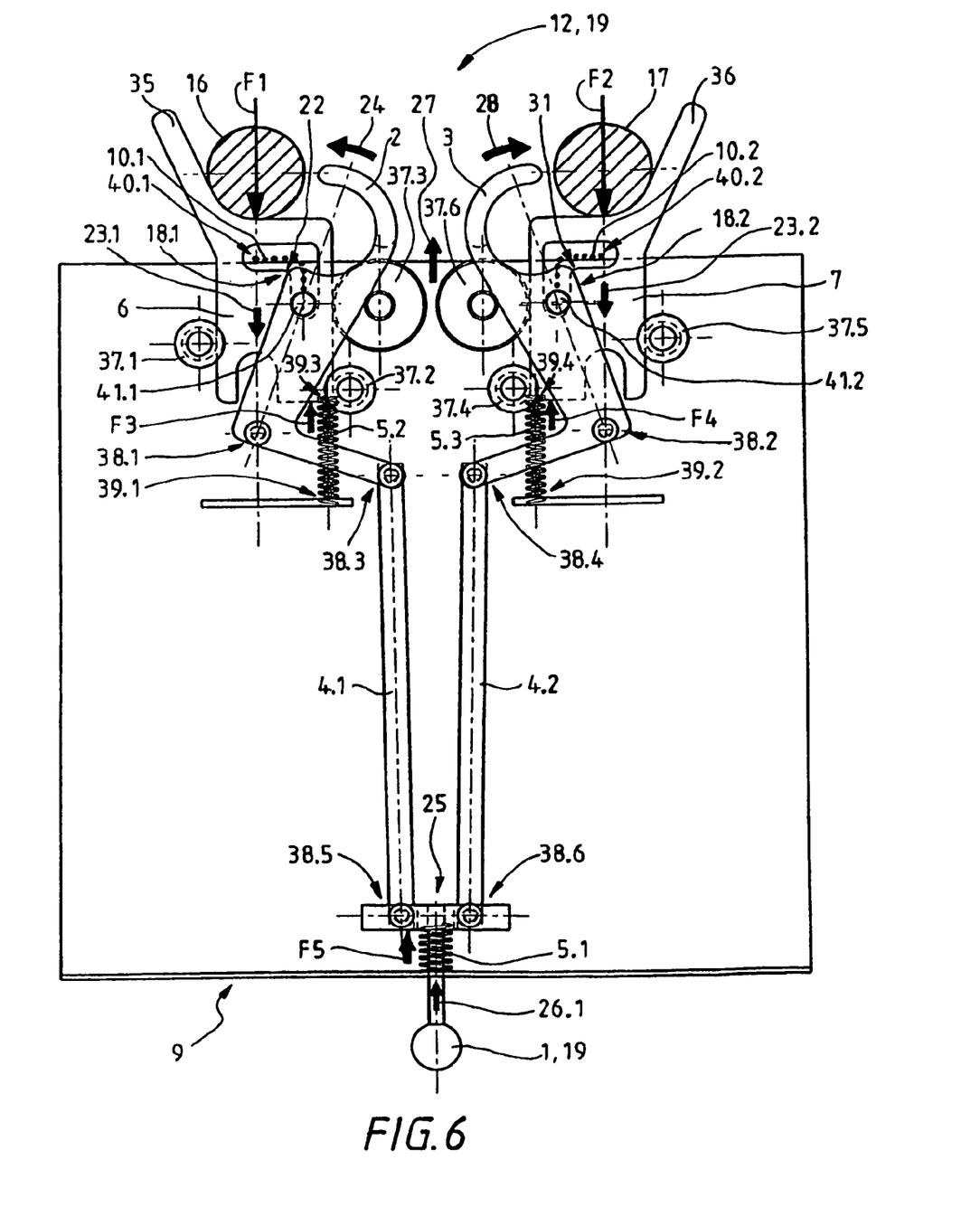
FIG. 6 shows a sectional view VI-VI according to FIG. 3 of the coupling device in an open position.

FIG. 6 shows a sectional view VI-VI according to FIG. 3 of the coupling device 12 in an opened, uncoupled position (open position 19 of the two jaws 2, 3), wherein a top side of a tabletop 34 of the cart 9 was removed. In order to couple both support rods 16, 17 to the coupling device 12, the transport cart 9 is initially moved to the position shown in FIG. 6, wherein the two fixing arms 35, 36, which are spread open from one another, have a centering function for both of these support rods 16, 17.

Each one of the two fixing arms 35, 36 has an extension of a first or second linear slide 6, 7, which receives a linear guide from a first, second, and third guide roller 37.1-37.3 or from a fourth, fifth, and sixth guide roller 37.4-37.6.

The first or second jaw 2, 3 is designed to swivel around a first or second joint 38.1, 38.2 in each case and is connected to a first or second pull rod 4.1, 4.2 via a third or fourth joint 38.3, 38.4 and connected to the control knob 1 via a fifth or sixth joint 38.5, 38.6.

Figure 7:
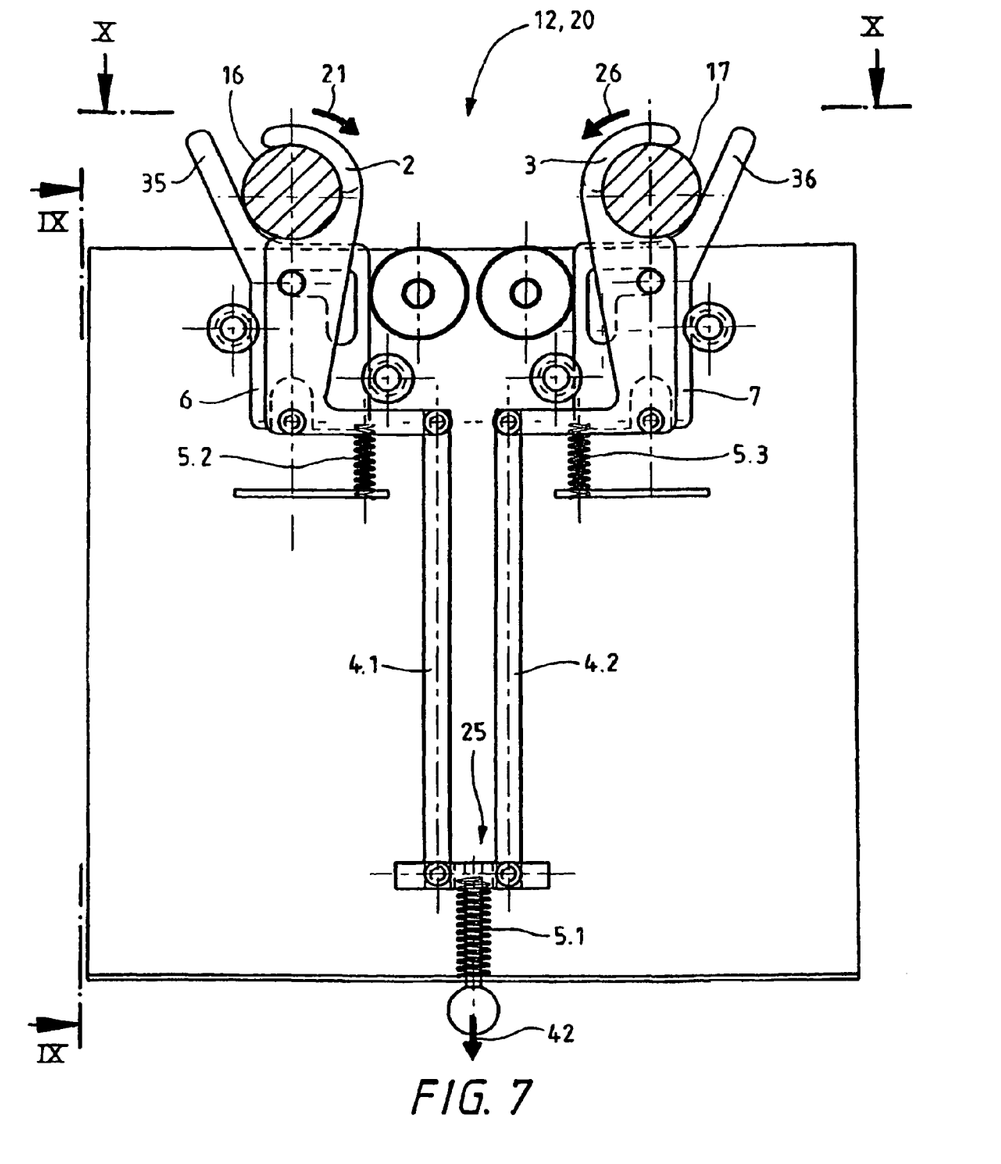
FIG. 7 shows the coupling device according to FIG. 6, but in a closed (coupled) position.

Movement (arrow 27) of the transport cart 9 against the first and the second support rod 16, 17 of the supply panel 13 results in an application of force F1 to the first linear slide 6 and an application of force F2 to the second linear slide 7, wherein both linear slides 6, 7 are moved inward almost simultaneously (arrow 23.1, 23.2) working against a smaller level of force F3 or F4 of the second or third compressing spring 5.2, 5.3. The jaws 2, 3 can each thereby swivel in with a snap (arrow 24, 28) via a first or second guide pin 41.1, 41.2 along a first or second L-shaped guide rocker 40.1, 40.2 via a path 10.1 or 10.2 represented by a dotted line and clamp each of the support rods 16, 17 once the first and second guide pin 41.1, 41.2 have passed beyond a first edge or a second edge 22, 31 of the first or second L-shaped-guide rocker 40.1, 40.2. (FIG. 7 shows this docking status.) The control knob 1 is moved inwards (arrow 26.1) via a spring force F5 of the first compressing spring 5.1. Thus, the docking procedure is visibly completed and the transport cart 9 is connected to the supply panel 14.

The compressing springs 5.2, 5.3 have a fixed first or second counter-support 39.1, 39.2 and correspond to a movable third or fourth counter-support 39.3, 39.4 on the first or second linear slide 6, 7.

Figure 8:
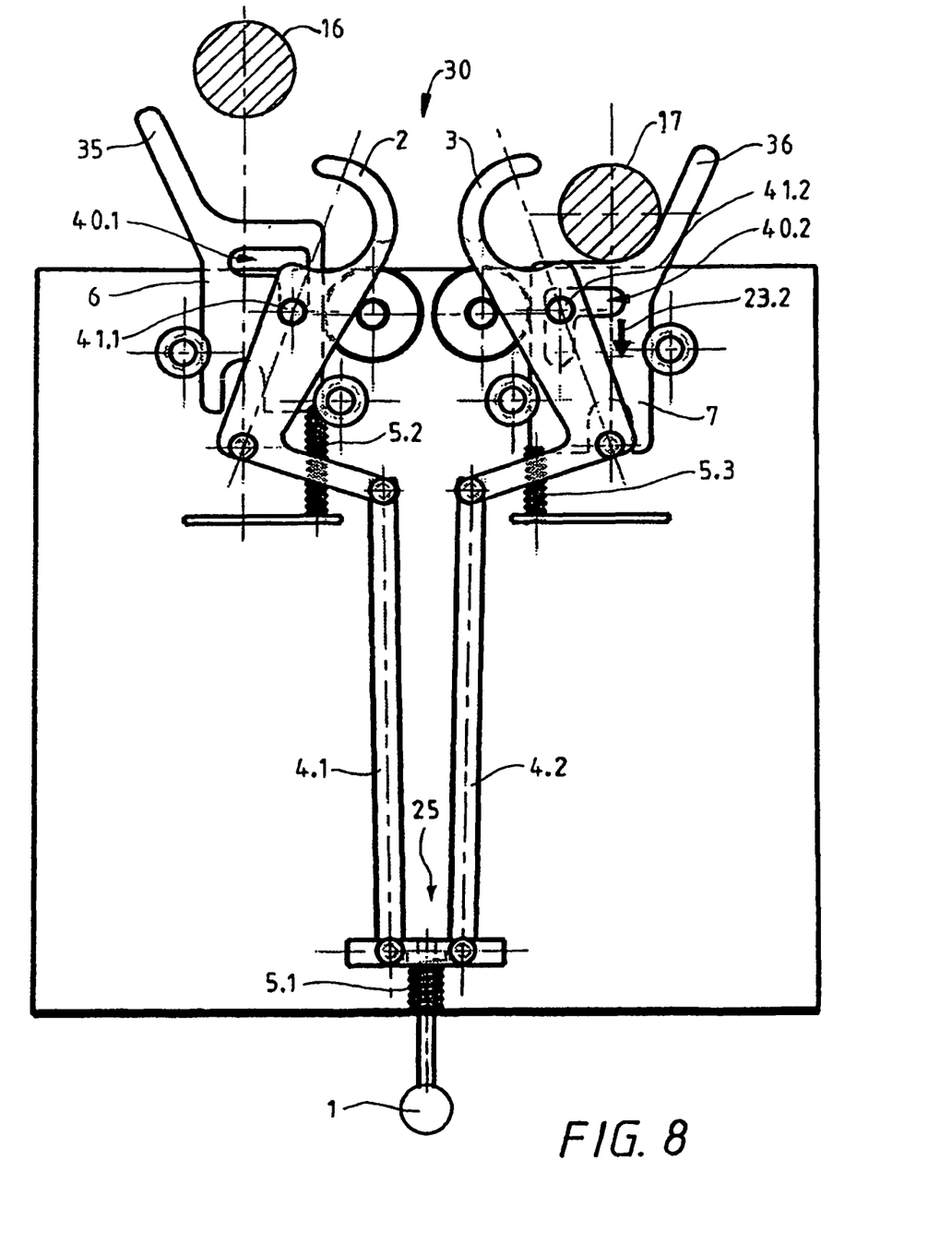
FIG. 8 shows the coupling device according to FIG. 6, but in an intermediate position.

If only one side is coupled by the user in a faulty coupling process (single-sided coupling) for the transport cart 9 and thus, e.g., only the second linear slide 7 moves inward on the right (arrow 23.2), the jaws 2, 3 of the coupling device 12 remain locked in their position 30, because, due to the coupling using an interlock device 25 from both jaws 2, 3 via pull rod 4.1 or 4.2, a release of swivel movement 24 or 28 cannot occur (FIG. 8).

In order to separate the coupling, the jaws 2, 3 of the coupling device 12 are opened via pulling (arrow 42, FIG. 7) on the control knob 1 of the pull rods 4.1, 4.2 of the coupling device 12. The compressing springs 5.2, 5.3 are then preloaded. The jaws 2, 3 of the coupling device 12 autonomously remain in this position (open position 19, FIG. 6), because the first and the second linear slides 6, 7 are extended and the jaws 2, 3 are thereby blocked, which means that they cannot execute swivel movement 24 or 28.

The connection with the structure 15 is disengaged via manual pulling 42 on the control knob 1 (FIG. 7), whereby the transport cart 9 can now be removed. In doing so, the jaws 2, 3 of the coupling device 12 are swiveled (arrow 21, 26) and automatically locked in their position (open position 19) as long as the transport cart 9 is removed from the support rods 16, 17. This position is achieved by the spring force F3 or F4 of the compressing springs 5.2, 5.3 that push both of the linear slides 6, 7 outwards as well as the L-shape of the guide rocker 40.1, 40.2. The coupling device 12 is thus prepared for a new coupling process.

Figure 9:
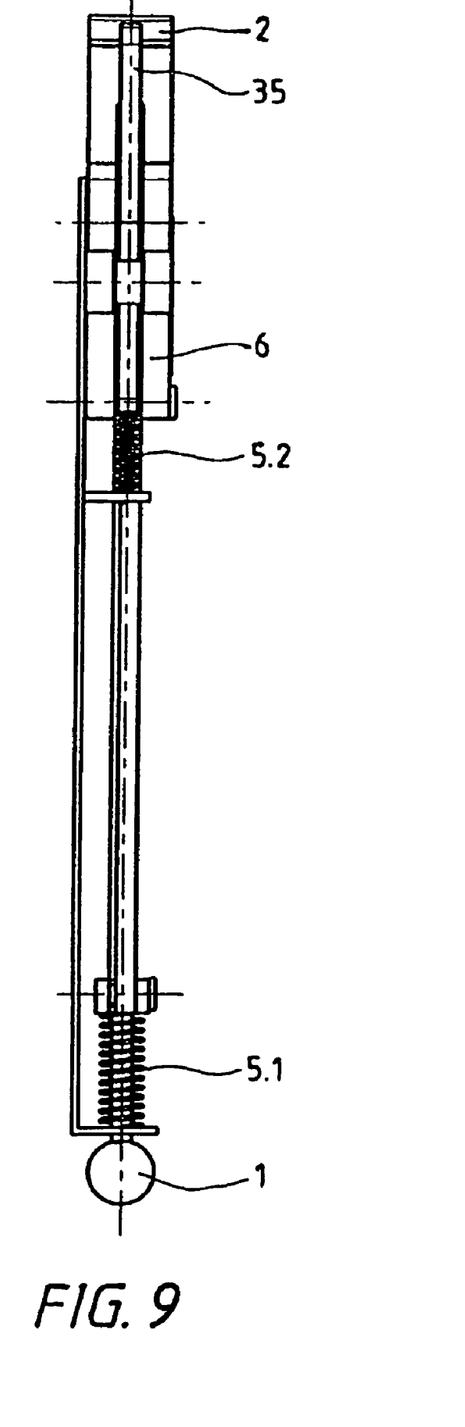
FIG. 9 shows a side view IX-IX of the coupling device according to FIG. 7.

FIG. 9 shows a side view IX-IX of the coupling device according to FIG. 7.

Figure 10:
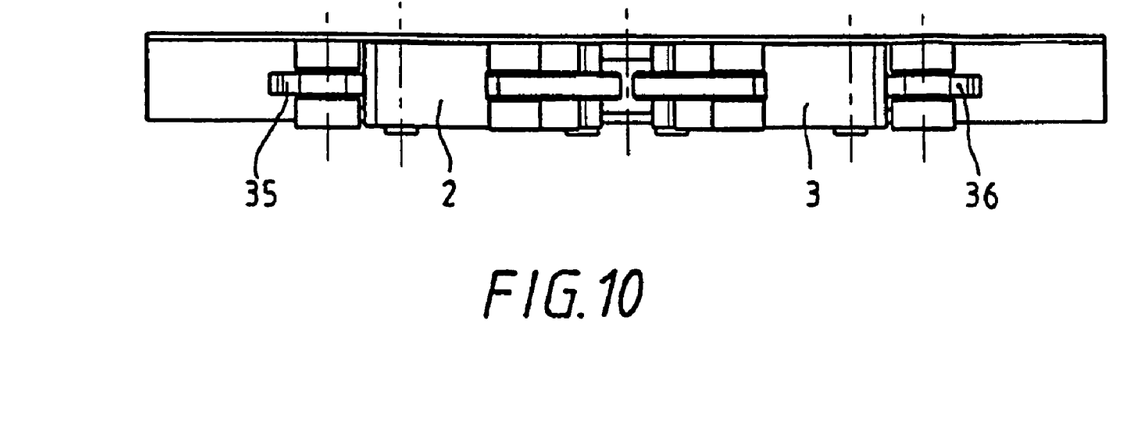
FIG. 10 shows a side view X-X of the coupling device according to FIG. 7.

FIG. 10 shows a side view X-X of the coupling device according to FIG. 7.

Figure 11:
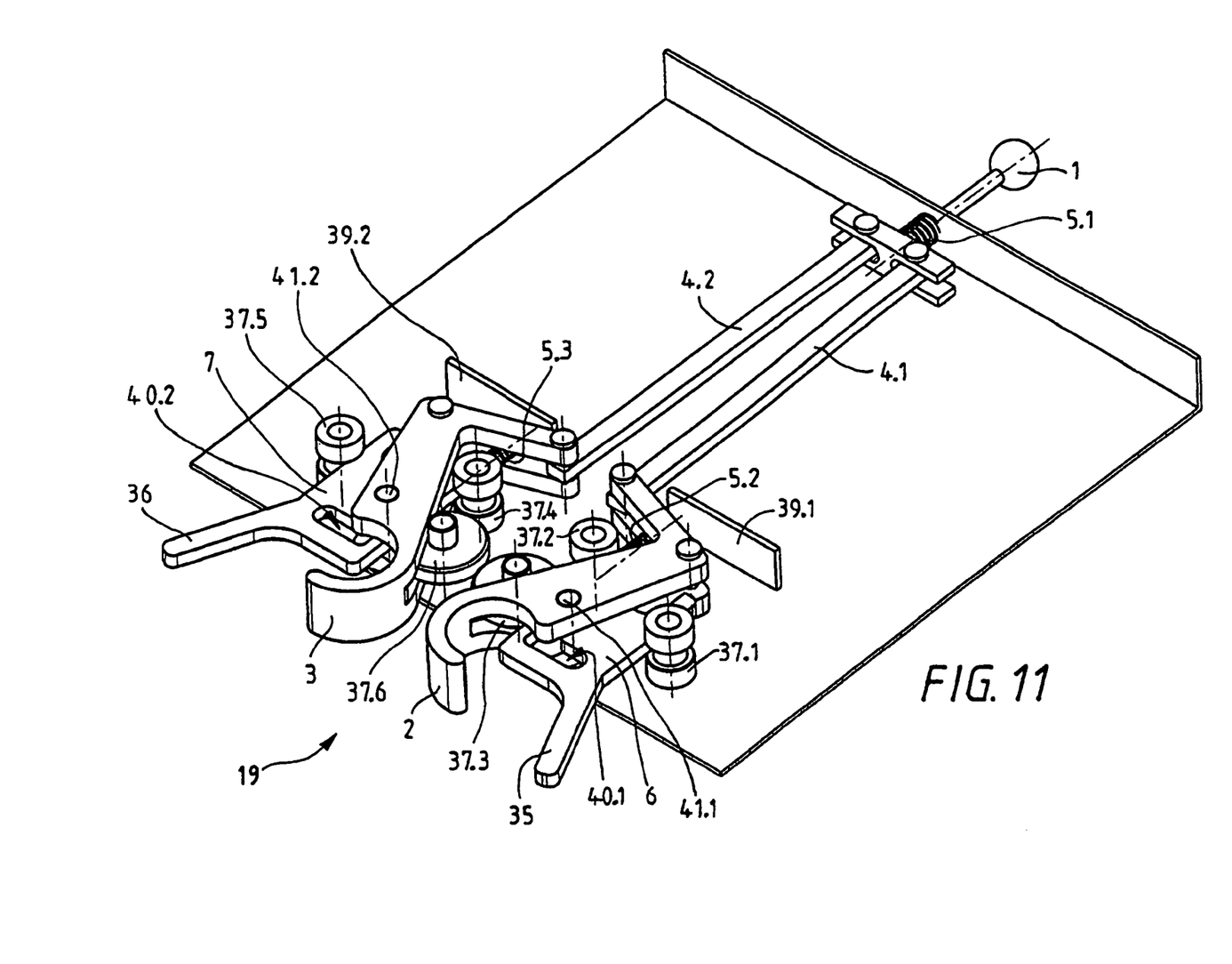
FIG. 11 shows a perspective view of the coupling device according to FIG. 6.

For improved viewing, FIG. 11 shows a perspective view of the coupling device according to FIG. 6, but without both of the support rods 16, 17.

Figure 12:
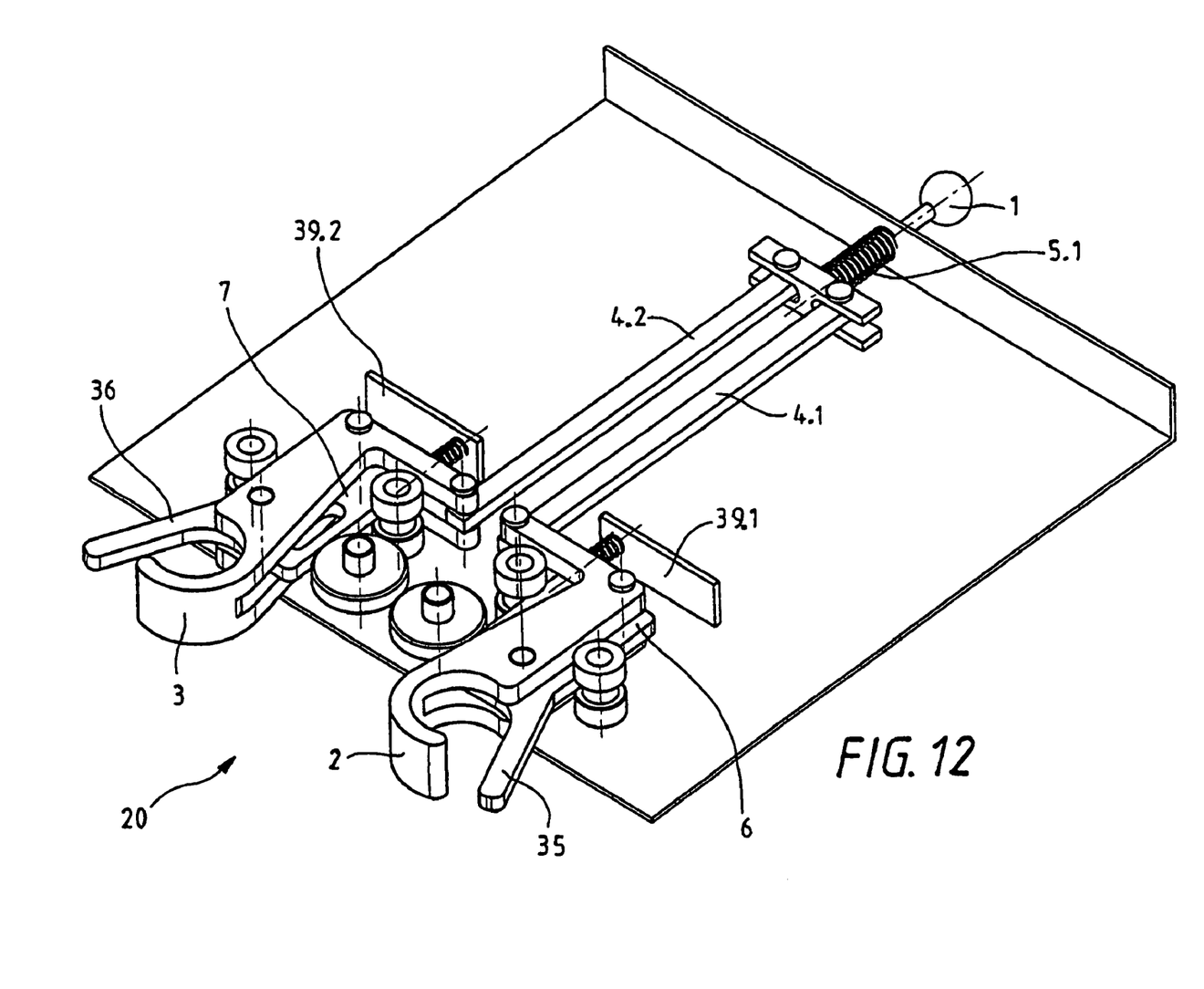
FIG. 12 shows a perspective view of the coupling device according to FIG. 7.

For improved viewing, FIG. 12 shows a perspective view of the coupling device according to FIG. 7, but without both of the support rods 16, 17.

PARTS REFERENCE LIST

1 Control knob
2 First jaw
3 Second jaw
4.1 First pull rod
4.2 Second pull rod
5.1-5.3 First through third compressing spring
6 First linear slide
7 Second linear slide
8 Supply connections
9 Transport cart
10.1 Path/guide pin 41.1
10.2 Path/guide pin 41.2
12 Coupling device
13 Supply panel
14 Ceiling mount
15 Structure
16 First support rod
17 Second support rod
18.1 First latching device
18.2 Second latching device
19 Open position
20 Closed position
21 Arrow/swivel movement
22 First edge
23.1 Arrow/movement inwards
23.2 Arrow/movement inwards
24 Arrow/swivel movement
25 Interlock device
26 Arrow/swivel movement
26.1 Arrow
27 Push
28 Arrow/swivel movement
29 Tray
30 Locking position
31 Second edge
32 Drip stand
33 Wheel
34 Tabletop
35 First fixing arm
36 Second fixing arm
37.1-37.6 First through sixth guide roller
38.1-38.6 First through sixth joint
39.1-39.4 First through fourth counter-support
40.1 First guide rocker
40.2 Second guide rocker
41.1 First guide pin
41.2 Second guide pin
42 Pulling direction
F1-F5 First through fifth compressing spring force The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 min".

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A coupling device of a transport cart, by means of which coupling device the transport cart is adapted to be attached to a structure of a supply panel for medical applications, wherein the supply panel can be positioned through a ceiling mount, the coupling device comprising a first jaw with a first latching device and a second jaw with a second latching device, the first and second jaws being adapted to be coupled to the structure of the supply panel, wherein, in order to enable coupling of the transport cart to the structure, each of the first jaw and the second jaw is adapted via the first latching device and the second latching device, respectively, to be locked into a closed position from a stopped, uncoupled open position upon mechanical pressure contact with the structure, wherein the first latching device and the second latching device are provided with an interlock device which prevents the first and second jaws from moving independently from the open position to the closed position.

2. The coupling device according to claim 1, wherein each of the first and the second latching devices has an L-shaped guide rocker that corresponds with a respective first or second guide pin.

3. The coupling device according to claim 2, wherein the first latching device and the second latching device respectively comprise a first linear slide and a second linear slide, and wherein each of the first and second linear slides includes the L-shaped guide rocker that interacts with the corresponding first or second guide pin provided on the first and second jaws.

4. The coupling device according to claim 2, wherein the first and second jaws are adapted to move between the open and closed positions once the first and second guide pins have passed beyond a first edge and a second edge, respectively, of the first and second L-shaped guide rocker.

5. The coupling device according to claim 1, wherein the coupling device exhibits a symmetrical construction.

6. The coupling device according to claim 1, wherein the first and second latching devices are interconnected by the interlock device.

7. A transport cart adapted to be coupled to a structure of a supply panel for medical applications, the transport cart comprising a coupling device having a first jaw with a first latching device and a second jaw with a second latching device, the first and second jaws being adapted to be coupled to the structure of the supply panel, wherein, in order to enable coupling of the transport cart to the structure, each of the first jaw and the second jaw is adapted via the first latching device and the second latching device, respectively, to be locked into a closed position from a stopped, uncoupled open position upon mechanical pressure contact with the structure, wherein the first latching device and the second latching device are provided with an interlock device which prevents the first and second jaws from moving independently from the open position to the closed position.

* * * * *